United States Patent [19]

Schroth et al.

[11] Patent Number: 4,849,008
[45] Date of Patent: Jul. 18, 1989

[54] ROOT CROP GROWTH PROMOTANTS

[75] Inventors: Milton N. Schroth, Orinda, Calif.;
Thomas J. Burr, Geneva, N.Y.

[73] Assignee: The Regents of the University of California, Oakland, Calif.

[21] Appl. No.: 899,757

[22] Filed: Aug. 21, 1986

Related U.S. Application Data

[63] Continuation of Ser. No. 404,103, Aug. 2, 1982, abandoned, which is a continuation-in-part of Ser. No. 932,909, Aug. 11, 1978, abandoned.

[51] Int. Cl.$^4$ .............................................. A01N 63/00
[52] U.S. Cl. ........................................... 71/77; 71/79; 435/876; 435/877
[58] Field of Search ..................... 71/77, 79; 435/876, 435/877

[56] References Cited

U.S. PATENT DOCUMENTS 159,847  1/1911  Coates
4,061,488  12/1977  Mann ..................................... 71/77

OTHER PUBLICATIONS

Avakyan et al. (1972) Chem. Abst. 77:440474e.
Burr et al., Proc. Am. Phytopath. Soc. (1977) 4:158 (Abstr.).
Burr et al., Phytopathology (1978) 68:1377–83.
Kloepper et al., Nature (1980) 286:885–86.
Kloepper et al., Current Microbiology (1980) 4:317–20.
Kloepper et al., Proc. IV. Int. Conf. Plant Pathogenic Bacteria (1978) vol. 2:879–82.
Kloepper et al., Phytopathology (1980) 70:1078–82.
Kloepper et al., Phytopathology (1981) 71:590–92.
Kloepper et al., Phytopathology (1981) 71:642–44.
Kloepper et al., Phytopathology (1981) 71:1020–24.
T. J. Burr & M. N. Schroth (1977) Phytopathology 67:1382–1387.
Chemical Abstracts 89:2872x.
Annual Meeting Abstracts (1976) Section 322, p. 273.

*Primary Examiner*—Catherine L. Mills
*Attorney, Agent, or Firm*—Bertram I. Rowland

[57] ABSTRACT

Methods and compositions for enhancing the yield of root crops, such as potatoes, sugar beets, radishes and the like, comprise treating the roots, plants, seeds, seed pieces, or soil in which they are to be planted, with a root crop growth promotant bacteria of the genus Pseudomonas.

10 Claims, No Drawings

ROOT CROP GROWTH PROMOTANTS

This is a continuation of Ser. No. 404,103 filed Aug. 2, 1982, now abandoned, which is a continuation-in-part of Ser. No. 932,909 in the names of Milton N. Schroth and Thomas J. Burr filed Aug. 11, 1978, for Root Crop Growth Promotants now abandoned.

BACKGROUND OF THE INVENTION

1. Field of the Invention

Agricultural growers and researchers are constantly seeking means to economically improve root crop yields. One increasingly popular method involves the use of so-called "beneficial" microorganisms which stimulate the plant growth and crop yield.

It has been known for many years that some soil microorganisms are beneficial to plant growth through the production of growth hormones, antibiotics which kill harmful soil microorganisms, and by aiding in the uptake of nutrients by the plants. For many years, researchers have attempted to exploit there beneficial microorganisms by adding them to planting soil directly or by applying them to seeds and roots. This practice has been commonly referred to as "bacterialization."

2. Description of the Prior Art

Avakyan, et al. (1972) Chem.Abst. 77:440474e discloses the treatment of peach seedlings with filtrate obtained from a culture of Pseudomonas fluorescens, inter alia, to promote the growth of peach trees. Phytopathology (1977) 67:1382-87, Proc. Am. Phytopath. Soc. (1977) 4:158 (Abstr.), Phytopathology (1978) 68:1377-83, Nature (1980) 286:885-86, Current Microbiology (1980) 4:317-20, Proc. IV. Int. Conf. Plant Pathogenic Bacteria (1978) Vol. 2: 879-82, Phytopathology (1980) 70:1078-82, Phytopathology (1981) 71:590-92, Phytopathology (1981) 71:642-44 and Phytopathology (1981) 71:1020-24, discuss various aspects of the treatment of root crop seeds with pseudononads. Phytopathology (1981) 71:866 (Abstr.) identifies certain strains of pseudomonads which are useful in the practice of the present invention.

SUMMARY OF THE INVENTION

A promotant comprising (a) at least one pseudomonad capable of promoting the growth of a root crop and (b) an agronomically acceptable carrier greatly enhances root crop production and inhibits certain root crop diseases. Since the commonly isolated pseudomonads have little effect on plant growth and yield, it is wholly unexpected that certain strains of Pseudomonas when applied to the root or in the vicinity of the root would produce such significant results.

DESCRIPTION OF THE SPECIFIC EMBODIMENT

Root crop production is enhanced and root crop diseases, such as root rot, are inhibited by treating the seeds, seed pieces, roots, or planting soil with naturally-occurring bacteria isolated from roots or tubers and selected for their ability to inhibit the growth of common plant pathogens. Such bacteria are subsequently introduced into the soil surrounding a root crop, usually at concentrations much higher than naturally present. The method is particularly useful for introducing such bacteria into soils where they are not naturally present.

Bacteria useful in the present invention may be identified by first isolating a large number of strains from the vicinity of healthy root crops, usually from the surfaces of such crops, by conventional methods. After incubation, these strains may be selected by antibiosis exhibited against a common root crop pathogen, such as Erwinra carotovara, which causes inhibition zones to appear about antagonistic colonies. Growth promotant strains may be further selected by their ability to promote the growth of crops under particular soil conditions.

Bacterial strains useful for the invention will be from the genus Pseudomonas, more usually strains of the species Pseudomonas putida and Pseudomonas fluorescens. Specific strains which have been identified include BK-1, TL-3, SH-5, A-1 (ATCC accession no. 39168), B-10 (ATCC accession no. 39169), E-6 (ATCC accession no. 39169). The first three of these strains (BK-1, TL-3 and SH-5) are on deposit with the U.S. Department of Agriculture, Agricultural Research Service in Peoria, Ill., without restriction and are available to the public. The strains were deposited on Aug. 7, 1978, and granted NRRL numbers B-11372, B-11373, and B-11374, respectively. The Culture Collection, having the designated acquisition numbers.

In general, the bacterial strains of the present invention are applied, alone or in combination with one or more other strains, to seeds, seed pieces or roots of root crops such as potatoes, sugar beets, radishes and the like, in concentrations from about $10^5$ to about $10^9$ cells/ml of an agronomically acceptable liquid carrier medium. A paste may be used to apply to the seeds at a concentration of $10^{10}$ cells/ml or greater. While it is preferred to apply the pseudonomads of the present invention directly to the seeds, seed pieces of roots prior to planting, the subject microorganisms can also be used to colonize soil in the area of planting prior to planting. In particular, they may be used to recolonize soil which has been fumigated or pasteurized.

The pseudomonads of this invention may be utilized effectively in diverse formulations, including agronomically acceptable adjuvants and carriers normally employed for facilitating the dispersion of active ingredients for agricultural applications, recognizing as known fact that the dosage, formulation, mode of application, and other variables may affect its activity in any given application. Thus, the previously described pseudomonads may be formulated as a suspension or dispersion, in aqueous or nonaqueous media, as a dust, as a wettable powder, as an emulsifiable concentrate, as a granule, or as any of several other known types of formulations, depending on the desired mode of application. These compositions may be applied as sprays, dust, or granules to the seeds, seed pieces, roots, plants, soil, or plant situs against which activity is desired.

In order to prevent compositions in the form of dust, granules, water dispersible powders, aqueous dispersions, or emulsions and dispersions in organic liquids, the carrier or diluent agent in such formulations may be a finely divided solid, an organic liquid, water, a wetting agent, a dispersing agent, or emulsifying agent, or any suitable combination of these. Generally, when liquids and wettable powders are prepared, a conditioning agent comprising one or more surface-active agents or surfactants is present in amounts sufficient to render a given composition containing the active material, the microorganism, dispersible in water or in oil. The pseudomonads are obtained as described above and cultured by standard fermentation procedures. To convert the desired pseudomonad to a form which will facilitate the preparation of the following described compositions, a slurry is prepared which is then dried into a primary, agronomically acceptable carrier such as vermiculite, whereby the microorganism is adsorbed onto the carrier. The microorganism, adsorbed onto the carrier, becomes the concentrate for preparing the desired composition. If desired, the slurry can be used as the concentrate for fungal antagonist compositions.

The surface active agent used in the invention can be a wetting, dispersing, or emulsifying agent which will assist dispersion of the effective composition. The surfaceactive agent or surfactant can include such anionic, cationic, and nonionic agents as have heretofore been generally employed in plant control compositions of similar types. Suitable surface-active agents are set forth, for example in "Detergents and Emulsifiers" 1971 Annual by John W. McCutcheon, Inc.

In general, 1–10% by weight of the surface-active agent will be used in compositions of this invention and ordinarily the amount of surface-active agent will range from 1–5% but may even be less than 1% by weight.

Additional surface-active agents can be added to formulations to increase the ratio of surfactants: active ingredients up to as high as 5:1 by weight. Such compositions may have a greater biological effectiveness than can be expected when the components are used separately. When used at higher ratios, it is preferred that the surfactant be present in the range of one-fifth to five parts surfactant for each one part of active agent. More specific formulations are disclosed in Examples 7 to 10, hereinafter.

The following examples further illustrate the present invention.

EXAMPLE 1

Isolation of Pseudomonads

Bacteria were isolated from the surface of freshly dug, healthy potato tubers and selected for their ability to exhibit antibiosis against *Erwinia carotovora*, (EC) in vitro. Isolations were made from potato cv., White Rose and Russet Burbank. Each tuber was washed in 100 ml sterile distilled water for approximately 10 min. Dilutions were then made from wash water, plated on King's medium B (KB) and incubated at 28° C. for 24 hr. After incubation, plates were sprayed with a 24 hr-old culture of Ecc and incubated an additional 24 hr at which time inhibition zones were apparent about antagonistic colonies.

Isolates were subsequently checked for antibiosis against Ecc, *E.carotovora var.* atroseptica (Eca) and the sugarbeet soft-rot Erwinia (25)***. They were also examined for their potential to rot potatoes by inoculating slices of cv. Russet Burbank with suspensions of approximately $10^7$ colony forming units (cfu)/ml of each isolate and incubating at 28° C. for 48 hr. Erwinia carotovora var. Carotovora (Ecc) strain SR-55 and Eca strain SR-150 were obtained from Dr. Arthus Kelman (University of Wisconsin, Madison), and sugarbeet Erwinia strain Sh-1 was isolated from a rotted beet from Shandon, Calif.

One hundred eight bacteria which exhibited antibiosis to Ecc in vitro were isolated from the surfaces of potato tubers. Antagonists were readily isolated from both cv. White Rose and Russet Burbank. Eighty-six were fluorescent Pseudomonas spp., twelve were Bacillus ssp., and ten were not readily identifiable to any particular group. All isolates which inhibited growth of Ecc also inhibited Eca, and the sugarbeet soft rot Erwinia. Eight Pseudomonas spp. and three Bacillus spp. rotted potato slices and were therefore unsuitable for seedpiece inoculation.

EXAMPLE 2

Greenhouse Screening of Antagonists

Ninety-seven strains of selected antagonistic bacteria were grown on KB for 48 hr, scraped from plates, and diluted to give suspensions of approximately $10^9$ cfu/ml. Five uniformly cut potato seedpieces cv. White Rose were dipped for 5 min. in each suspension and planted in pots containing loamy sand field soil obtained from Shafter, Calif. To reduce variability, apical and stem end portions were removed from seed tubers and only single eye pieces were planted. Fresh weights of roots and shoots were taken from 4 week-old plants, or generally one week after emergence of shoots. These experiments were repeated three times with strains that stimulated plant growth.

Two Pseudomonas strains, TL-3 and BK-1 usually stimulated plant growth in the greenhouse. Percent increases in fresh weight of shoot and root systems ranges from 0 to 367% (Table 1). Growth responses were observed with soils from different locations in Kern County and with UC mix (3)***, but were not observed in peat soil obtained from Stockton delta area.

Pseudomonas strains TL-3 and BK-1 were identified using the techniques and substrates according to Stanier et al. (24)* as modified by Sands et al. (23)* A number of nitrogen and carbon sources were used in addition to those listed by the previously mentioned authors. Pseudomonas strains TL-3 and BK-1 fit the general descriptions of *P. fluorescens* ad *P. putida*, respectively, using 140 different tests. However, neither TL-3 nor BK-1 resemble the descriptions of the known biotypes of either species and presumably are representatives of undescribed biotypes.

TABLE 1

| | | | Effect of bacterial treatments on the development of potatoes in greenhouse trials. | | |
|---|---|---|---|---|---|
| Trial | Cultivar | Soil type[a] | Number of reps./treat. | Strains[b] tested | Average fresh wt. of root and shoot (g) | % increase over checks |
| 1 | White Rose | UC mix | 20 | Check | 0.3 | |
| | | | | BK-1 | 1.4 | 367*[c] |
| | | | | TL-3 | 1.1 | 267* |
| | | | | Ac-1 | 1.2 | 300* |
| | | | | S-1-B | 0.6 | 100 |
| 2 | White Rose | UC mix | 10 | Check | 11.4 | |
| | | | | BK-1 | 13.8 | 21* |
| | | | | TL-3 | 14.4 | 26* |
| | | | | Ac-1 | 12.2 | 7 |
| | | | | TL-10 | 8.4 | −26* |
| | | | | Mixture | 12.8 | 12 |
| 3 | White Rose | Loamy sand[d] | 20 | Check | 3.78 | |

TABLE 1-continued

Effect of bacterial treatments on the development of potatoes in greenhouse trials.

| Trial | Cultivar | Soil type[a] | Number of reps./treat. | Strains[b] tested | Average fresh wt. of root and shoot (g) | % increase over checks |
|---|---|---|---|---|---|---|
| | | | | BK-1 | 5.64 | 49** |
| | | | | TL-3 | 4.46 | 18 |
| | | | | Ac-1 | 4.38 | 26 |
| | | | | TL-10 | 2.73 | −38 |
| 4 | White Rose | Loamy sand | 12 | Check | 2.86 | |
| | | | | TL-3 | 5.25 | 84* |
| 5 | White Rose | Loamy sand | | Check | 0.8 | |
| | | | | TL-3 | 2.5 | 213** |
| 6 | White Rose | Loamy sand | 12 | Check | 0.93 | |
| | | | | TL-3 | 1.8 | 94** |
| 7 | White Rose | Peat | 12 | Check | 0.95 | |
| | | | | TL-3 | 1.09 | 15[e] |
| 8 | Kennebec | UC mix | 20 | Check | 4.22 | |
| | | | | BK-1 | 5.93 | 41** |
| | | | | TL-3 | 7.13 | 69** |
| | | | | AC-1 | 5.48 | 30 |
| | | | | TL-10 | 5.54 | 31 |
| | | | | Mixture | 6.12 | 45** |

[a]Loamy sand soil was obtained from a potato field near Shafter, California. Peat soil was obtained from a potato field near Stockton, California. Each listing of loamy sand represents soil taken from a different location in Kern County.
[b]Strains (TL-3, TL-10 and BK-1) are fluorescent Pseudomonas spp. which were isolated from tubers grown at Tulelake and Bakersfield, California, respectively. Strain S-1-B is Bacillus spp. isolated from a tuber grown at Bakersfield, California. Isolate Ac-1 is an *Erwinia quercina* strain obtained from Dr. M. N. Schroth.
[c]*denotes significance (P 0.05);
**denotes (P = 0.01).
[d]Statistically non-significant results were obtained in 3 other experiments.

EXAMPLE 3

Establishment of Antagonist on Seedpiece Surfaces and In the Rhizospheres of Treated Plants Pseudomonas strains TL-3 and BK-1 were isolated from freshly dug tubers, cv. Russet Burbank, from Tulelake, and cv. White Rose from Bakersfield, Calif., respectively. Potato seedpieces, cv. White Rose, were dipped for 5 minutes in suspensions containing approximately $10^9$ cfu/ml of TL-3 or BK-1. Seedpieces were then placed on paper towels in the laboratory and sampled at various time intervals to determine the effect of air-drying on the survival of the inoculum. Laboratory temperature and relative humidity averaged 24° C. and 20% RH during the air-drying period. Population determinations were made by removing tissue with a number 5 cork borer (0.785 cm² surface area) contiguous to eyes from treated seedpieces and placing them in 100 ml sterile distilled water. Serial water dilutions were subsequently made and plated on KB. One plug from each of three seedpieces were sampled at each time interval and three dilution plates were made from each plug. Plates were incubated for 24 hr at 28° C. Preliminary investigations showed that this amount of sampling was sufficient to provide consistent data.

The ability of the pseudomonads to survive on seedpieces and roots in field soil was determined by previously described inoculation and sampling procedures. This and the following work was performed with seedpieces planted in loamy sand soil in the greenhouse. The sampling of roots for the presence of pseudomonads was made by excising one cm root sections from the tips and mid sections of three roots per plant and washing them individually along with some clinging soil particles with 1 ml sterile distilled water. One-tenth ml of these suspensions was then plated on three KB plates. The population of pseudomonads on roots of treated and non-treated seedpieces were followed up to 8 weeks. No attempt was made to determine the precise location of the bacteria, i.e., rhizoplane versus rhizosphere.

Populations of strain TL-3 on the surface of potato seedpieces consistently averaged $10^7$ cfu/0.785 cm² immediately after seedpieces were dipped in suspensions of approximately $10^9$ cfu/ml. Populations declined rapidly if allowed to air dry and were about $5 \times 10^3$ cfu/0.785 cm² after 4 weeks.

EXAMPLE 4

Bacterial Survival in Moist Soil

The effect of soil moisture on bacterial survival on seedpieces was tested by planting seedpieces in a loamy sand soil from Shafter, Calif. with soil matrix water potentials of −16.1, −2.8 and −1.7 bars and air dried. Moisture determinations were made on a C-51 sample chamber psychrometer (Wescor, Inc., Logan, Utah 84321). Survival capability of the bacteria was determined using the same population sampling methods previously described.

The planting of potato seedpieces into soils of low soil water potentials adversely affected the survival of TL-3. Populations on seedpieces differed nearly 1000 fold 96 hr after planting into soils with water potentials of −16.1 to −1.7 bars.

Strains TL-3 and BK-1 apparently spread from the inoculated seedpieces to the roots, as they were detected in the rhizospheres of potato plants in field soil harvested one month after planting. The bacteria were present along all sections of roots at high populations although greatly variable, and were the predominant rhizosphere bacteria present on treated plants after two months (Table 2).

Identification of the pseudomonads in rhizospheres of treated plants was relatively simple because of their predominance and their characteristic colony morphologies and fluorescence on KB. The immuno-fluorescent staining procedure also was effective for identifying isolate TL-3. Of 15 rhizosphere Pseudomonas spp. isolated obtained from control plants, none reacted positively to the prepared fluorescent antibody.

TABLE 2

Survival of Pseudomonas strain TL-3 on potato roots in field soil in the greenhouse.[a]

| Age of plant (wks) | Soil type[b] | No. of plants sampled | Length of root piece (mm) | Average TL-3 pop. × $10^{-2}$ on roots[c] | |
|---|---|---|---|---|---|
| | | | | root tips | Mid root |
| 2 | loamy sand | 9 | 4 | 1602 ± 1675 | |
| 4 | loamy sand | 6 | 1 | 128 ± 107 | 90 ± 97 |
| 8 | loamy sand | 5 | 1 | | 24 ± 28 |
| 4 | peat | 11 | 1 | | 146 ± 218 |

[a]Plants originated from seedpieces dipped in a suspension of strain TL-3 containing approximately $10^9$ colony-forming units/ml.
[b]Loamy sand soil was obtained from a potato field near Bakersfield, California. Peat soil was obtained from a potato field near Stockton, California.
[c]Root sections of 1 or 4 cm in length were placed in 1 ml water, agitated and 0.1 ml plated on King's medium B.

EXAMPLE 5

Determination of Potato Soft-Rot Inhibition

The ability of Pseudomonas strains TL-3 and BK-1 to inhibit soft-rot of potato caused by *Erwinia cartovora* (Ecc) was determined using potato discs, cv. Kennebec cut with a number 12 cork borer (3.14 cm² surface area) and sliced approximately 1 cm thick. Discs were dipped in suspension of pseudomonads of various concentrations for 5 minutes. Six discs were then placed in each Large Petri dish (14 cm diameter, bottom) with moistened filter paper to maintain a most environment. The discs were then either inoculated immediately with Ecc or incubated at 28° C. for 2 or 4 hr at which time known quantities of Ecc were spread on the discs, using sterile disposable capillary pipettes. Water dipped controls were also inoculated at each time interval. Potato discs were subsequently incubated for 24 hr at 28° C. and differences in soft-rot development were noted. Discs which did not exhibit a rot in 24 hr did not rot at later time periods.

from which serial water dilutions were made and plated on the media.

Pseudomonas strains TL-3 and BK-1 reduced the incidence and severity of potato soft-rot caused by Ecc. All concentrations of pseudomonads inhibited soft-rot development when Ecc inoculum levels were $4 \times 10^2$ cfu/potato disc and below (Table 3). As pathogen levels increased, however, greater populations of TL-3 were needed to prevent rot; soft-rot development was not prevented by concentrations of the Pseudomonas when Ecc levels reached $4 \times 10^5$ cfu/potato disc. Almost identical data was obtained when isolate BK-1 was used.

Isolations from Pseudomonas-treated potato discs which remained healthy revealed the presence of substantial populations of both Pseudomonas and Ecc 24 and 48 hr after inoculation. Ecc populations, however, were approximately 100 fold less than on discs inoculated alone with the same quantities of Ecc. These data suggest that the cause of soft-rot inhibition may not be entirely due to a lethal effect of the Pseudomonas on the pathogen.

TABLE 3

Inhibition of potatoe soft-rot by Pseudomonas strain TL-3.

| | Incubation time prior to inoculation with Eerwinia (hr)[a] | | | | | | | | |
|---|---|---|---|---|---|---|---|---|---|
| | 0 | | | | | | 2 | | |
| Erwinia conc.[b] (colony forming units/disc) | TL-3 concentration (colony forming units/ml)[b] | | | | | | | | |
| | Check | $1.0 \times 10^5$ | $1.0 \times 10^6$ | $1.0 \times 10^7$ | $1.0 \times 10^8$ | $1.0 \times 10^9$ | Check | $1.0 \times 10^5$ | $1.0 \times 10^6$ |
| 0 | — | — | — | — | — | — | — | — | — |
| 4 | — | — | — | — | — | — | NT[c] | — | — |
| $4 \times 10^1$ | +[d] | — | — | — | — | — | — | — | — |
| $4 \times 10^2$ | ++ | — | — | — | — | — | — | ++ | — |
| $4 \times 10^3$ | ++ | — | — | ++ | — | + | + | — | + |
| $4 \times 10^4$ | ++++ | ++++ | +++ | ++ | + | + | +++ | +++ | ++ |
| $4 \times 10^5$ | ++++ | NT | +++ | ++ | ++ | ++ | ++++ | NT | +++ |

| | Incubation time prior to inoculation with Eerwinia (hr)[a] | | | | | | | |
|---|---|---|---|---|---|---|---|---|
| | 2 | | | 4 | | | | |
| Erwinia conc.[b] (colony forming units/disc) | TL-3 concentration (colony forming units/ml)[b] | | | | | | | |
| | $1.0 \times 10^7$ | $1.0 \times 10^8$ | $1.0 \times 10^9$ | Check | $1.0 \times 10^5$ | $1.0 \times 10^6$ | $1.0 \times 10^7$ | $1.0 \times 10^8$ | $1.0 \times 10^9$ |
| 0 | — | — | — | — | — | — | — | — | — |
| 4 | — | — | NT | — | — | — | — | — | NT |
| $4 \times 10^1$ | — | — | — | — | — | — | — | — | — |
| $4 \times 10^2$ | — | — | — | + | — | — | — | — | — |
| $4 \times 10^3$ | — | — | — | + | + | — | — | — | — |
| $4 \times 10^4$ | ++ | + | — | ++ | ++ | ++ | ++ | + | + |
| $4 \times 10^5$ | ++ | ++ | ++ | ++++ | NT | +++ | + | + | + |

[a]Potato discs were dipped in various concentrations of antagonists and inoculated with *E. carotovora* var. cartovora immediately or incubated 2 or 4 hr at 28° C. prior to inoculation.
[b]All bacteria were grown on King's medium B, and water suspensions of various concentrations were made for inoculations of potato discs.
[c]NT denotes concentrations which were not tested.
[d]Severity of rot is denoted by: + = 25% of disc rotted, ++ = 50%, +++ = 75%, ++++ = 100%.

Discs that were dipped in strain TL-3 and Ecc and did not rot were examined for changes in populations of TL-3 and Ecc at 24 and 48 hr after inoculation. Populations of TL-3 and Ecc were determined on KB and polygalacturonic acid-tergitol medium (6)***, respectively. Discs were washed in 10 ml sterile distilled water

EXAMPLE 6

Effect of Pseudomonads in Increasing Potato Yields

Nine replicated field experiments were made to test the effectiveness of various bacterial species on potato yields. Strains TL-3, TL-10 and TL12 were nonpectoytic, fluorescent Pseudomonas spp. and were isolated from cv. Russett Burbank potatoes grown at Tulelake, Calif. Strain BK-1, a fluorescent Pseudomonas sp., and strain S-1-B, a Bacillus sp., were isolated from cv. White Rose potatoes grown at Shafter, Calif. *Bacillus subtilis* A-13 and *Erwinia quercina* AC-1 were obtained from Dr. K. F. Baker and M. N. Schroth, respectively. All of the above strains exhibited antibiosis to Erwinia soft-rot spp. in vitro except AC-1, which was tested because of the growth-promoting characteristic it exhibited when inoculated onto carrot slices (16)***. Forty-hr-old inocula for field trials were obtained on KB in large plastic petri dishes, whereas Bacillus spp. were cultured on potato dextrose agar. Seedpieces were dipped for 5 min in suspensions of approx. $10^9$ cfu/ml prepared by adding inoculum from 15 large Petri dishes to 6 liters of water. Seedpieces were then placed in large polyethylene bags and immediately taken to the field for planting. Commercial planting procedures were followed in all plots and tubers were mechanically harvested unless otherwise specified. In early experiments tubers were graded and yield increases were based on the increases of US No. 1 tubers. In later tests, total weight was used since grading did not reveal any differences in the size and quality of tubers among the various trials.

Potato yields were increased up to 33% by inoculation of seedpieces with Pseudomonas spp. (Table 4). Strain TL-3 was responsible for the greatest increases in yield in two plots. Yield increases of 20 to 24% or greater were usually necessary before significance could be demonstrated at the 5% level because of the variation within the plots. In the Idaho plot, however, significance was achieved at the 5% level with a 13% increase in yield. This plot and the plot at Stockton, Calif., were dug by machines and hand harvested, while all other plots were machine harvested.

Increases in yields were not obtained with plots located on peat soils at Tulelake and Stockton, Calif. This paralleled greenhouse studies in that no effect was obtained when seedpieces were planted in pots containing peat soils.

TABLE 4

Effect of bacterial treatments on potato yields in field plot experiments.

| Field plot location and year[a] | Cultivar | Soil type | Strains[b] tested | Plot row length | Average yield (kg/plot) | % increase over checks |
|---|---|---|---|---|---|---|
| Shafter, Ca. Spring 1975 | White Rose | loamy sand | Check | 15.2 m | 29.6 | |
| | | | TL-3 | | 36.8 | 24**[c] |
| | | | TL-10 | | 32.9 | 11 |
| | | | Ac-1 | | 34.4 | 16** |
| | | | A-13 | | 33.2 | 12 |
| Shafter, Ca. Fall 1975 | White Rose | loamy sand | Check | 15.2 m | 4.5 | |
| | | | TL-3 | | 4.2 | −7 |
| | | | BK-1 | | 6.0 | 33** |
| | | | Ac-1 | | 3.5 | −22 |
| | | | S-1-B | | 3.8 | −16 |
| Shafter, Ca. Spring 1976 | White Rose | loamy sand | Check | | 22.9 M | 76.7 |
| | | | TL-3 | | 78.4 | 2 |
| | | | TL-10 | | 75.6 | −1 |
| | | | Ac-1 | | 76.1 | −1 |
| | | | BK-1 | | 81.0 | 6 |
| | | | Mixture | | 74.3 | −3 |
| Arvin, Ca. | Kennebec | loamy sand | Check | 22.9 | 48.7 | |
| | | | TL-3 | | 57.5 | 18* |
| | | | TL-10 | | 49.5 | 0 |
| | | | Ac-1 | | 47.9 | 0 |
| | | | BK-1 | | 50.3 | 3 |
| | | | Mixture | | 53.0 | 9 |
| Bakersfield, Ca. Spring 1976 | White Rose | Loamy sand | Check | 22.9 | 56.0 | |
| | | | TL-3 | | 67.4 | 20* |
| | | | TL-10 | | 63.7 | 14 |
| | | | Ac-1 | | 66.1 | 18 |
| | | | BK-1 | | 63.3 | 13 |
| | | | Mixture | | 54.1 | −3 |
| Tulelake, Ca. Fall 1975 | Russet Burbank | loamy sand | Check | 30.4 m | 82.8 | |
| | | | TL-3 | | 77.0 | −7 |
| | | | TL-10 | | 95.6 | 15 |
| | | | Ac-1 | | 83.4 | −1 |
| | | | A-13 | | 76.0 | −9 |
| | | | TL-12 | | 70.0 | −14 |
| Tulelake, Ca. Fall 1976 | Russet Burbank | peat | Check | 30.4 | 71.2 | |
| | | | TL-3 | | 74.8 | 5 |
| | | | TL-10 | | 69.4 | −3 |
| | | | Ac-1 | | 69.0 | −4 |
| | | | BK-1 | | 72.6 | 2 |
| | | | Mixture | | 74.0 | 4 |
| Minidoka, Idaho Fall 1976 | Russet Burbank | sandy loam | Check | 24.3 m | 84.0 | |
| | | | TL-3 | | 95.4 | 14** |
| | | | TL-10 | | 89.7 | 7 |
| | | | BK-1 | | 93.0 | 11** |
| | | | Fungicide (Maneb) | | 86.8 | 3 |
| Stockton, Ca. Winter 1976 | White Rose | peat | Check | 22.9 | 72.3 | |
| | | | TL-3 | | 82.4 | 14 |
| | | | TL-10 | | 79.0 | 9 |
| | | | BK-1 | | 78.4 | 8 |

TABLE 4-continued

Effect of bacterial treatments on potato yields in field plot experiments.

| Field plot location and year[a] | Cultivar | Soil type | Strains[b] tested | Plot row length | Average yield (kg/plot) | % increase over checks |
|---|---|---|---|---|---|---|
| | | | TL-3 | | 77.9 | 9 |

[a] A Latin square of randomized block design with 4 to 6 replications/treatment were used in each plot.
[b] Isolates (TL-3, TL-10, TL-12) and BK-1 are nonpectolytic fluorescent Pseudomonas spp. which were isolated from tubers grown at Tulelake and Bakersfield, California, respectively. Isolates S-1-B and A-13 are Bacillus spp. isilated from a tuber grown at Bakersfield, California, ad obtained from Dr. K. F. Baker, respectively. Isolate Ac-1 is an *Erwinia quercina* isolate obtained from Dr. M. N. Schroth.
[c] ** denotes significance at (P = 0.05), * denotes (P = 0.10).

EXAMPLE 7

Wettable Powders

Wettable powders are water-dispersible compositions containing the active material, an inert solid extender, and one or more surfactants to provide rapid wetting and to prevent heavy flocculations when suspended in water. The inert extenders which are preferred for use in the wettable powders of this invention containing the active compounds are of mineral origin.

Extenders suitable for the wettable powder formulations of this invention are the natural clays, diatomaceous earth and synthetic mineral fillers derived from silica and silicate. Most preferred fillers for this invention are kaolinites, attapulgite clay, montmorillonite clays, synthetic silica, synthetic magnesium silicate and calcium sulfate dihydrate.

Among the more preferred surfactants are the nonionic and anionic types. They are most suitable for the preparation of dry, wettable products of this invention and dispersants. Occasionally a liquid, nonionic compound which is primarily an emulsifier, may serve as both wetter and dispersant.

Most preferred wetting agents are alkylbenzene and alkylnapthalene sulfonates, sulfated fatty alcohols, amines or acid amides, long chain esters of sodium isothionate, esters of sodium sulfosuccinate, sulfated or sulfonated vegetable oils, and ditertiary acetylenic glycols. Preferred dispersants are methyl cellulose, polyvinyl alcohol, lignine sulfonates, polymeric alkylnapthalene sulfonates, sodium napthalene sulfonates, polymethylene bisnapthalene sulfonate and sodium-N-methyl-N-(long chain acid) taurates.

Wetting and dispersing agents in these preferred wettable powder compositions of the invention are usually present at concentrations of from about 0.5 weight percent to 5 weight percent. The inert extender then completes the formulation. Where needed, 0.1 weight percent of the extender may be replaced by a corrosion inhibitor or an antifoaming agent or both.

Thus, wettable powder formulations of the invention will contain from about 25 to 90 weight percent active material, from 0.5 to 2.0 percent wetting agent, from 0.25 to 5.0 weight percent dispersant, and from 9.25 to 74.25 weight percent inert extender, as these terms are described above.

When the wettable powder contains a corrosion inhibitor or an antifoaming agent or both, the corrosion inhibitor should not exceed about 1 percent of the composition, and the antifoaming agent should not exceed about 0.5 percent by weight of the composition, both replacing equivalent amounts of the inert extender.

EXAMPLE 6

Dusts

Dusts are dense powder compositions which are intended for application in dry form. Dusts are characterized by their free-flowing and rapid settling properties so that they are not readily windborne to areas where their presence is not desired. They contain primarily an active ingredient and a dense, free-flowing solid extender. Their performance is sometimes aided by the inclusion of a wetting agent, and convenience in manufacture frequently demands the inclusion of an inert absorptive grinding aid.

The wettable powder as described above can also be used in the preparation of dusts. While such wettable powders can be used directly in dust form, it is more advantageous to dilute them by blending with the dense dust diluent. In this manner, dispersing agents, corrosion inhibitors, and antifoam agents may also be used as components of a dust.

Thus, the dust compositions of this invention can comprise from about 0.5 to 20.0 weight percent active ingredient, 5 to 25 weight percent filler, 0 to 1.0 weight percent wetting agent and from about 30 to 90 weight percent dense, free-flowing extender, as these terms are used herein. Such dust formulations can contain, in addition, minor amount of dispersants, corrosion inhibitors, and antifoam agents derived from the wettable powders used to make the dust.

EXAMPLE 9

Emulsifiable Oils

Emulsifiable oils are usually solutions or suspensions of active material in nonwater miscible solvents together with a surfactant and/or emulsifier.

For compositions of this invention, emulsifiable oil compositions can be made by mixing the active ingredient with an organic solvent and surfactant. Suitable surfactants are those ionic or nonionic agents known to the art as emulsifying agents.

Emulsifying agents most suitable for the emulsifiable oil compositions of this invention are long chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty rosin acids, fatty alkylol amide condensates, calcium and amine salts of fatty alcohol sulfates, oil soluble petroleum sulfonates, or preferably mixtures of these emulsifying agents. Such emulsifying agents should comprise from about 1 to 10 weight percent of the total composition. As described above, however, up to 5 parts of emulsifying agent for each part of active ingredient can be used.

Thus, emulsifiable oil compositions of the present invention can consist of from about 10 to 50 weight percent active ingredients, about 40 to to 82 percent solvents, and about 1 to 10 weight percent emulsifier, as these terms are defined and used above.

EXAMPLE 10

Granules

Granules are physically stable, particulate compositions containing mycelium, sclerotia or spores of this invention which adhere to or are distributed through a basic matrix of a coherent, inert carrier with microscopic dimensions. In order to aid leaching of the active ingredient from the granule, a surfactant can be present.

The inert carrier is preferably of mineral origin, and suitable carriers are natural clays, some pyrophyllites and vermiculite. Suitable wetting agents can be anionic or nonionic.

For the granule composition of this invention, most suitable carriers are of two types. The first are porous, absorptive pre-formed granules, such as preformed and screened granular attapulgite or heat expanded granular, screened vermiculite. On either of these, a suspension of the active agent can be sprayed and will be absorbed at concentrations up to 25 weight percent of the total weight. The second type are initially powdered kaolin clays, hydrated attapulgite or bentonite clays in the form of sodium, calcium or magnesium bentonites. Water-soluble salts such as sodium salts may also be present to aid in the disintegration of the granules in the presence of moisture. These ingredients are blended with the active components to give mixtures that are granulated, followed by drying to yield formulations with the active component distributed uniformly throughout the mass. Such granules can also be made with 25 to 30 weight percent active component but more frequently a concentration of about 10 weight percent is desired for optimum distribution. The granular compositions of this invention are believed to be most useful in a size range of 15-30 mesh.

The most suitable wetting agents for the granular compositions of this invention depend upon the type of granule used. When pre-formed granules are sprayed with active material in liquid form, the most suitable wetting agents are nonionic, liquid wetters miscible with the solvent. These are more generally known in the art as emulsifiers and comprise alkyl-aryl polyether alcohols, alkyl polyether alcohols, polyoxyethylene sorbitan fatty acid esters, polyethylene glycol esters with fatty or rosin acids, fatty alkylol amide concentrates, oil soluble petroleum or vegetable oil sulfonates, or mixtures of these. Such agents will usually comprise up to about 5 weight percent of the total composition.

When the active ingredient is first mixed with a powdered carrier and subsequently granulated, liquid nonionic wetters can still be used, but it is usually preferable to incorporate at the mixing stage, one of the solid, powdered anionic wetting agents such as those previously listed for the wettable powders. Such agents should comprise aabout 0 to 2 weight percent of the total composition.

Thus, the preferred granular formulations of this invention comprise about 5 to 30 weight percent active material, about 0 to 5 weight percent wetting agent, and about 65 to 95 percent inert mineral carrier, as these terms are used herein.

EXAMPLE 11

Effect of Other Strains of Pseudomonas on Rootzone Populations of Erwinia carotovora Various strains of Pseudomonas were tested in three geographically diverse field plots. Dried inocula were prepared containing $10^8$ cfu/g as described by Kloepper et al., Phytopathology (1981) 71:590-96 and were dusted onto potato seed pieces immediately prior to planting. Control seed pieces were dusted with powders prepared the same way except water was substituted for the bacterial suspensions. Field 1 was a sandy loan, pH 7.2, near Shafter, Calif., and fields 2 and 3 were peat soils, pH 7.0, in Tulelake, Calif. The strains tested was A-1, B-10, TL3B2, and BK-1 in Field 1; B-10 and E-6 in field 2; and A-1 and B-10 in field 3.

Field plots were arranged in randomized blocks with 4 row plots each 7.6 m (25 ft.) long. Each treatment was replicated 5 times. Cultivar White Rose was used in field 1 and cultivar Netted Gem in fields 2 and 2.

Populations of Ecc were determined 2 wks prior to harvest by sampling 50 cm root per plant. Three plants were randomly selected per replication. Roots were agitated in 10 ml sterile distilled water and serial 10-fold dilutions were prepared to $10^{-3}$. Tenth ml aliquots of each dilution were plated onto the medium described below.

The medium used was a modification of Miller-Schroth *Erwinia amylovora* medium (Miller, et al., Phytopathology (1972) 66:367-70) with lactose substituted for Mannitol, 5 g oxoid bile salts substituted for sodium taurocholate, and with nicrotinic acid deleted. The pH was adjusted to 7.2 making the medium blue-green prior to autoclaving. The medium may be stored up to 3 months and melted prior to pouring plates. Plates were allowed to set 12 to 24 hr after pouring and then overlayed with sodium polypectate. Sodium polypectate was prepared by dissolving 1 g disodium EDTA in one liter of distilled water and mixing with a suspension of 20 g sodium polypectate (manufactured by Sunkist Growers Inc., Ontario, Calif. and available from WARF Institute, Inc., Madison, Wis. 53707) and 60 ml of 95% ethanol. The pH was adjusted with 1N NaOH while stirring and straining out lumps which formed when NaOH was added.

Populations of Ec on roots from pseudomonad-treated seed pieces were 95 to 100% less than on roots of control plants (P=0.05) at harvest time in all 3 fields. (Table 5). Neither soil type nor soil pH seemed to affect efficacy of the pseudomonad in displacing or preventing root colonization of Ec. Pseudomonad strain TL3B2 as the only strain which did not cause in a significant reduction in Ec root-zone populations.

EXAMPLE 12

Effect of Pseudonomads on *Eriwinia cartovora* Investion of Daughter Tubers

Inocula were prepared as before and used in three fields. Fields 4 and 5 were sandy loams, pH 7.2, near Shafter, Calif., and cultivar White Rose was used at both sites. Field 6 was a silt loam, pH 5.2, near Gold, Pa., and cultivar Katahdin was used. Strains tested were BK1, B10 and a mixture of B10 and TL3B1 in field 4; BK1 was a mixture of BK1, TL3B1 and B10 in field 5; and A1, E6, and a mixture of A1, B10, BK1, TL3A, TL3B1, TL3B2, and E6 in field 6. Controls were included as previously described. All treatments were replicated six times in four row plots as previously described.

After harvest, 20 to 30 tubers were randomly selected from each replication of each treatment in each field and were individually wrapped as previously described to induce formation of soft rot pockets. Pectolytic bacteria detected on the Erwinia medium were periodically removed and tested as described above to confirm identification as Ecc. The percentage of daughter tubers from which Ecc. was recovered was recorded for each treatment.

TABLE 5

Reduction in *Erwinia carotovora* populations on roots of potato treated with plant growth-promoting rhizobacteria in field tests.

| Field number location, and soil type | Seed piece treatment[a] | Average *Erwinia carotovora* population cfu/cm[b] | Percentage reduction relative to control |
|---|---|---|---|
| 1. Shafter, CA Sandy loam | Control | 41 | — |
| | A-1 | 1* | 97* |
| | B-10 | 0* | 100* |
| | TL3B2 | 16 | 61 |
| | BK-1 | 0.8* | 98* |
| | | LSD 0.05 = 32 | |
| 2. Tulelake, CA Peat | Control | 4660 | — |
| | B-10 | 52* | 99* |
| | E-6 | 188* | 96* |
| | | LSD 0.05 = 932 | |
| 3. Tulelake, Peat | Control | 312 | — |
| | A-1 | 31* | 90* |
| | B-10 | 16* | 95* |
| | | LSD 0.05 = 58 | |

[a]Strains are fluorescent pseudomonads applied to seed pieces in a dried powder formulation (Kloepper et al. (1980) Phytopathology 70:1078-82) prior to planting.
[b]Colony forming units per cm of root; average of 50 cm root per sample with 5 replications.
*Statistically significant reduction compared to control at the indicated level of significance.

Root colonization by the pseudomonads of the present invention resulted in reductions in the percentage of daughter tubers infested with Ecc (Table 6) ranging from 28 to 92% compared to control plants. The level of significance varied in each of the 3 fields from P=0.10 to P 0.01. One treatment in each field consisted of a mixture of 2 or more strains and the reductions in daughter tuber infestation of Ecc were similar to treatments of a single strain.

TABLE 6

Reduction in the percentage of daughter tubers infested with *Erwinia carotovora* following seed piece treatments with plant growth-promoting pseudomonad in field tests.

| Field number location, and soil type | Seed piece treatment[a] | Average *Erwinia carotovora* population cfu/cm[b] | Percentage reduction relative to control |
|---|---|---|---|
| 4. Shafter, CA 1980 sandy loam | Control | 32 | — |
| | BK1 | 14* | 56* |
| | B10 | 15* | 53* |
| | B10 + TL3B1 | 15* | 53* |
| | | LSD 0.10 = 16 | |
| 5. Shafter, CA | Control | 18 | — |
| | BK1 | 10* | 44 |
| | BK1 +, TL3B1 + B10 | 6* | 67 |
| | | LSD 0.07 = 8 | |
| 6. Gold, PA 1981 silt loam | Control | 25 | — |
| | A1 | 18 | 28 |
| | E6 | 2* | 92* |
| | Mixture[c] | 3* | 88* |
| | | LSD 0.01 = 11 | |

[a]Strains are fluorescent pseudomonads applied to seed pieces in a dried powder formulation (16) prior to planting.
[b]Average of 6 replications with 20 to 30 tubers per application.
[c]Mixture in field 6 contained A1, B10, BK1, TL3A, TL3B1, TL3B2, and E6.
*Indicates statistically significant reduction relative to control at the indicated level of significance.

In accordance with the subject invention, a simple and environmentally acceptable method is provided for enhancing the growth of root crops. By employing particular strains naturally occurring pseudomonads, the population of other native root zone microflora which can exert a negative effect upon plant growth, including common pathogens such as *E. carotovora*, may be reduced. Such reduction, in turn, has a beneficial effect on plant growth.

Although the foregoing invention has been described in some detail by way of illustration and example for purposes of clarity of understanding, it will be obvious that certain changes and modifications may be practiced with the scope of the appended claim.

What is claimed is:

1. A root crop growth promotant comprising (a) at least one pseudomonad selected to promote the growth of a root crop and (b) an agronomically acceptable carrier, wherein the pseudomonad is selected from the group comprising Pseudomonas strains BK-1, TL-3, SH-5, A-1, B-10, and E-6.

2. A promotant as in claims 1 wherein the pseudomonad is present in the carrier at a concentration effective to promote growth when applied to seeds before planting.

3. A promotant as in claim 1, wherein the effective concentration is in the range from about $10^5$ to $10^9$ cells/ml.

4. A promotant as in claim 2 in the form of a wettable powder.

5. A promotant as in claim 2 in a dust.

6. A promotant as in claim 2 in granular form.

7. A promotant as in claim 2 in the form of an emulsifiable oil.

8. A promotant as in claim 2, wherein the pseudomonad is present in the carrier at a concentration higher than required to be effective in promoting growth and may be mixed with additional agronomically acceptable carrier before use.

9. A method for improving the yield of root crops comprising applying an effective amount of the promotant of claims 1 to a root crop seed prior to the planting the seed.

10. A method for improving the yield of root crops comprising applying an effective amount of the promotant of claims 1 to the soil where a root crop seed is to be planted.

* * * * *

UNITED STATES PATENT AND TRADEMARK OFFICE
CERTIFICATE OF CORRECTION

PATENT NO. : 4,849,008

DATED : Jul. 18, 1989

INVENTOR(S) : Milton N. Schroth, Orinda, Calif.; Thomas J. Burr, Geneva, N.Y.; and Joseph W. Kloepper, Georgetown, Ontario, Canada It is certified that error appears in the above-identified patent and that said Letters Patent is hereby corrected as shown below:

On the title page inventors should read

-- Inventors: Milton N. Schroth, Orinda, Calif.;
            Thomas J. Burr, Geneva, N.Y.;
            Joseph W. Kloepper, Georgetown, Ontario, Canada--

Signed and Sealed this

Ninth Day of October, 1990

*Attest:*

HARRY F. MANBECK, JR.

*Attesting Officer*        *Commissioner of Patents and Trademarks*